United States Patent [19]
Hirata et al.

[11] Patent Number: 5,348,932
[45] Date of Patent: Sep. 20, 1994

[54] SYNERGISTIC HERBICIDAL COMPOSITION COMPRISING TRIAZINE HERBICIDES AND EITHER DICLOFOP OR FENOXAPROP WITH FENCHLORAZOLE

[75] Inventors: Toshihiro Hirata; Shin-ichiro Ogawa, both of Sodegaura, Japan

[73] Assignee: Idemitsu Kosan Company Limited, Tokyo, Japan

[21] Appl. No.: 70,549

[22] Filed: Jun. 1, 1993

[30] Foreign Application Priority Data

Jun. 8, 1992 [JP] Japan .................................. 4-171529

[51] Int. Cl.$^5$ ...................... A01N 25/32; A01N 43/68
[52] U.S. Cl. ................................. 504/106; 504/135
[58] Field of Search ................................. 504/106, 135

[56] References Cited

U.S. PATENT DOCUMENTS

| | | | |
|---|---|---|---|
| 3,954,442 | 5/1976 | Becker et al. | 71/108 |
| 4,130,413 | 12/1978 | Handte et al. | 71/90 |
| 4,844,731 | 7/1989 | Takematsu et al. | 71/93 |
| 4,932,998 | 6/1990 | Takematsu et al. | 71/93 |
| 5,169,425 | 12/1992 | Takematsu et al. | 71/88 |
| 5,234,893 | 8/1993 | Hirata et al. | 504/133 |

FOREIGN PATENT DOCUMENTS

| | | |
|---|---|---|
| 0174562 | 3/1986 | European Pat. Off. . |
| 0411153 | 2/1991 | European Pat. Off. . |
| 0464518 | 1/1992 | European Pat. Off. . |
| 0467204 | 1/1992 | European Pat. Off. . |
| 0469406 | 2/1992 | European Pat. Off. . |
| 0471221 | 2/1992 | European Pat. Off. . |
| 2223894 | 5/1972 | Fed. Rep. of Germany . |
| 53-40767 | 4/1978 | Japan . |
| 63-51379 | 3/1988 | Japan . |
| 4-77403 | 3/1992 | Japan . |
| 4-89409 | 3/1992 | Japan . |
| 4-95004 | 3/1992 | Japan . |
| 4-99703 | 3/1992 | Japan . |
| 4-235105 | 8/1992 | Japan . |
| WO90/09378 | 8/1990 | PCT Int'l Appl. . |
| WO92/16101 | 10/1992 | PCT Int'l Appl. . |
| 1423006 | 1/1976 | United Kingdom . |
| 1548847 | 7/1979 | United Kingdom . |

OTHER PUBLICATIONS

*The Agrochemicals Handbook*, 3rd ed. "Diclofop," Fenchlorazole, Fenoxaprop, Fenoxaprop—P. 1991.
Chemical Patents Index Basic Abstracts Journal, Section C, Week 8750, Feb. 17, 1988, Derwent Publications Ltd., London, GB; Class C, AN 87-353293/50 of JP-A-62 258 309, Nov. 10, 1987.
U.S. Pat. Appl. Ser. No. 07/582,835 filed Oct. 5, 1990.

*Primary Examiner*—Richard L. Raymond
*Assistant Examiner*—S. Mark Clardy
*Attorney, Agent, or Firm*—Frishauf, Holtz, Goodman & Woodward

[57] ABSTRACT

Herbicidal compositions comprising, as active ingredients, a triazine compound of the formula (I):

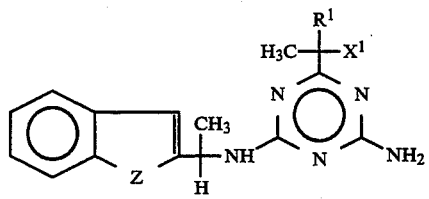

wherein Z is oxygen, sulfur or

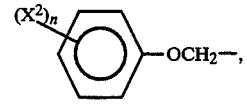

$X^2$ is methyl or fluorine,
n is 0 to 2,
$R^1$ is hydrogen or methyl, and
$X^1$ is fluorine or chlorine, and
(i) a mixture of (a) an aryloxyphenoxy herbicide, or an optical isomer thereof, of the formula (II):

(Abstract continued on next page.)

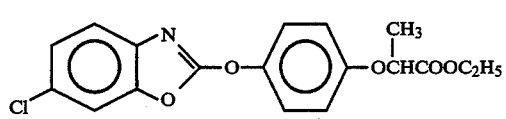
(II)
and (b) a safener for crop injury of the formula (III):
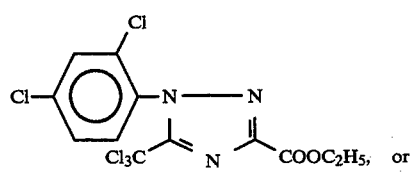
(III)
(ii) an aryloxyphenoxy herbicide of the formula (IV):
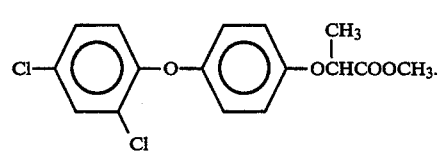
(IV)
The herbicidal compositions have a synergistic herbicidal effect against a wide spectrum of weeds, without incurring crop injury.
13 Claims, No Drawings

SYNERGISTIC HERBICIDAL COMPOSITION COMPRISING TRIAZINE HERBICIDES AND EITHER DICLOFOP OR FENOXAPROP WITH FENCHLORAZOLE

FIELD OF THE INVENTION

The present invention relates to a herbicidal composition comprising a triazine derivative and a mixture composed of a particular aryloxyphenoxy herbicide and a particular safener for crop injury as active ingredients and also to a herbicidal composition comprising a triazine derivative and a particular aryloxyphenoxy herbicide as active ingredients.

BACKGROUND OF THE INVENTION

Heretofore, various herbicides have been developed to contribute toward promoting the agricultural producibility and for energy-saving. However, since some herbicides have been used for a long period of time, weeds which could hardly be blighted or exterminated by such herbicides are increasing. Therefore, realization of herbicides having a broader herbicidal spectrum and being effective to combat even such troublesome weeds is desired. In addition, in order to solve the problem of environmental pollution by conventional herbicides, development of herbicides having a higher activity is also desired. Moreover, in order to control weeds emerging non-uniformly over a long period of time, it has been desired to develop herbicides having an excellent residual activity and having flexibility of treatment to exhibit effectiveness, even though the treatment is performed over a long period from preemergence, to a wide range of growing stage of weeds.

Under the situation, it was already found that particular novel haloalkyl-having triazine derivatives show a high herbicidal effect against troublesome weeds both by soil treatment and by foliage treatment without phytotoxicites of Gramineae crops, and especially that such derivatives show an excellent herbicidal effect against weeds in paddy fields (International Patent Application Laid-Open No. WO 90/09378). The present inventors further made earnest studies so as to improve the herbicidal activity of the triazine derivatives.

SUMMARY OF THE INVENTION

As a result, it has been found that a composition comprising a triazine derivative and a mixture composed of a particular aryloxyphenoxy herbicide and a particular safener for crop injury and also a composition comprising the triazine derivative and a particular aryloxyphenoxy herbicide, both show an excellent synergistic herbicidal activity which could not be anticipated from the properties of the individual ingredients, and that the compositions exhibit an high herbicidal effect even at a low dosage and have a wide range of herbicidal spectrum. On the basis of the findings, the present invention has been completed.

Specifically, the present invention first provides a herbicidal composition comprising, as active ingredients, a triazine derivative of a general formula (I):

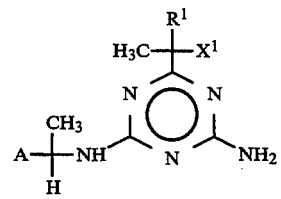

where A represents a group of a formula (a):

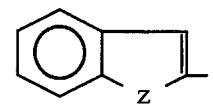

where Z represents an oxygen atom or a sulfur atom, or represents a group of a formula (b):

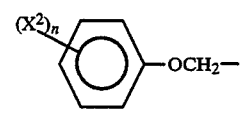

where $X^2$ represents a methyl group or a fluorine atom; and n represents an integer of from 0 to 2; $R^1$ represents a hydrogen atom or a methyl group; and $X^1$ represents a fluorine atom or a chlorine atom; and a mixture composed of an aryloxyphenoxy herbicide (including its optical isomer) of a formula (II):

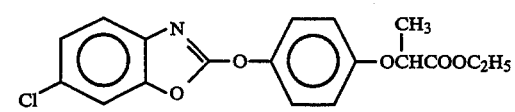

and a safener for crop injury of formula (III):

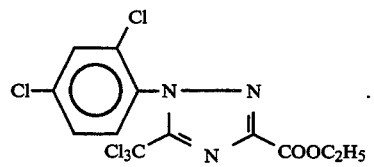

Secondly, the present invention also provides a herbicidal composition comprising, as active ingredients, a triazine derivative of a general formula (I):

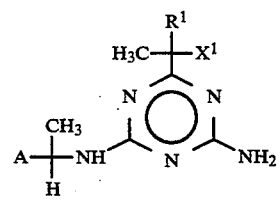

where A, $R^1$ and $X^1$ have the same meanings as mentioned above; and an aryloxyphenoxy herbicide of a formula (IV):

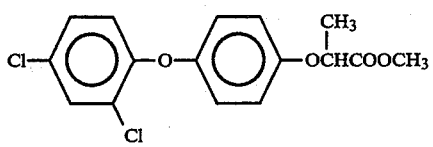

DETAILED DESCRIPTION OF THE INVENTION

The first herbicidal composition of the present invention comprises, as active ingredients, a triazine derivative of the above-mentioned general formula (I) and a mixture composed of an aryloxyphenoxy herbicide of the above-mentioned formula (II) and a safener for crop injury of the above-mentioned formula (III).

Specific examples of triazine derivatives of formula (I) are mentioned below, which, however, are not limitative.

They are 2-amino-4-[1-(benzofuran-2'-yl)ethylamino]-6-(α-fluoro, α-methylethyl)-s-triazine of formula:

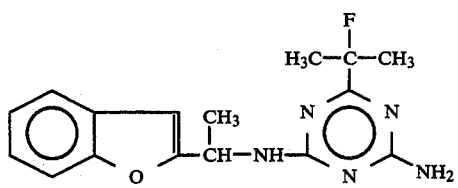

2-amino-4-[1-(benzofuran-2'-yl)ethylamino]-6-(α-fluoroethyl)-s-triazine of formula:

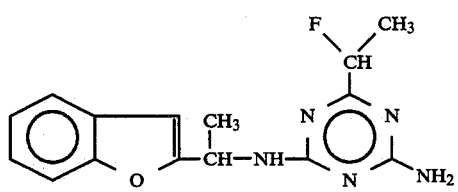

2-amino-4-[1-(benzothiophen-2'-yl)ethylamino]-6-(α-fluoro, α-methylethyl)-s-triazine of formula:

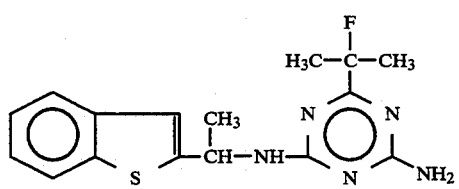

2-amino-4-(α-fluoro, α-methylethyl)-6-[2-(3',5'-dimethylphenoxy)-1-mehtylethylamino]-s-triazine of formula:

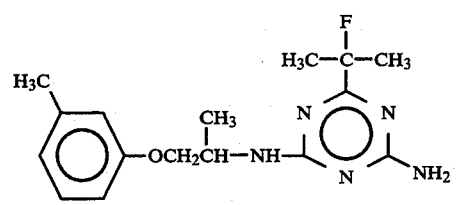

2-amino-4-(α-fluoro, α-methylethyl)-6-[2-(3'-fluorophenoxy)-1-methylethylamino]-s-triazine of formula:

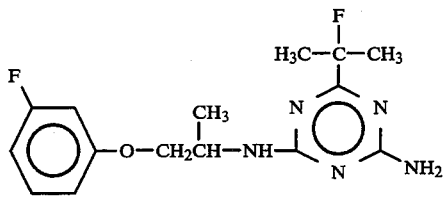

2-amino-4-(α-chloro, α-methylethyl)-6-[2-(3',5'-dimethylphenoxy)-1-methylethylamino]-s-triazine of formula:

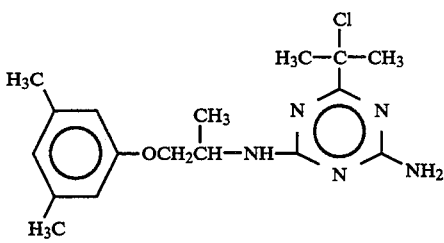

and 2-amino-4-(α-fluoro, α-methylethyl)-6-[2-(3',5'-dimethylphenoxy)-1-methylethylamino]-s-triazine of formula:

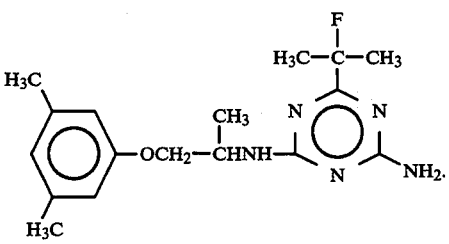

Such triazine derivatives of formula (I) can be produced by various methods. Among these methods, advantageous methods are described in International Patent Application Laid-Open No. WO 90/09378. The disclosure of the laid-open specification is referred to for the details of them.

As mentioned above, the first herbicidal composition of the present invention comprises, as active ingredients, a triazine derivative of the above-mentioned general formula (I) and a mixture composed of an aryloxyphenoxy herbicide of the above-mentioned formula (II) and a safener for crop injury of the above-mentioned formula (III).

The aryloxyphenoxy herbicide of formula (II) is concretely ethyl 2-[4-(6-chloro-2-benzoxazolyl-oxy)-phenoxy]propionate or its optical isomer. This may be obtained by known methods (Japanese Patent Application Laid-Open No. 53-40767).

The aryloxyphenoxy herbicide of formula (II) has a herbicidal effect to a wide range of Gramineae weeds and is used for broadleaf crops such as soybean and cotton. However, the herbicidal effect of the herbicide to broadleaf weeds is insufficient, while the herbicide could not be used for Gramineae crops as it causes crop injury to them. When the herbicide is mixed with the safener for crop injury of formula (III), then it may be used as a herbicide for a Gramineae weeds in wheat.

The safener for crop injury of formula (III) is ethyl 1-(2,4-dichlorophenyl)-5-trichloromethyl-1H-1,2,4-triazole-3-carboxylate. A mixture of the herbicide of formula (II) and the safener for crop injury of formula (III) is sold by Hoechst under the trade name of CHEE-TAH.

The first herbicidal composition of the present invention comprises, as active ingredients, a triazine derivative of formula (I) and a mixture composed of an aryloxyphenoxy herbicide of formula (II) and a safener for crop injury of formula (III), and the proportion of them is not always specifically defined. The composition shows an excellent synergistic herbicidal effect, having a broadly varying proportion of the ingredients. In general, it is preferred that the ratio of (triazine derivative)/(mixture of aryloxyphenoxy herbicide of formula (II) and safener for crop injury of formula (III)) is from 10/1 to 1/10 by weight.

The ratio of the aryloxyphenoxy herbicide of formula (II) to the safener for crop injury of formula (III) may be from 1/1 to 8/1, preferably from 2/1 to 4/1.

The second herbicidal composition of the present invention comprises a triazine derivative of the above-mentioned general formula (I) and an aryloxyphenoxy herbicide of the above-mentioned formula (IV).

The aryloxyphenoxy herbicide of formula (IV) is methyl (I)-2-[4-(2,4-dichlorophenoxy)phenoxy]propionate (known in German Patent Application Laid-Open (DOS) No. 2,223,894) and is sold, for example, as Hoegrass (trade name) by HOEGRASS.

The aryloxyphenoxy herbicide of formula (IV) has a wide range of herbicidal effect against Gramineae weeds and is used for Gramineae crops, such as barley or wheat, and also for broadleaf crops, but it's herbicidal effect to broadleaf weeds is insufficient.

The second herbicidal composition of the present invention comprises, as active ingredients, a triazine derivative of formula (I) and an aryloxyphenoxy herbicide of formula (IV), and the proportion of them is not always specifically defined. The composition shows an excellent synergistic herbicidal effect, having a broadly varying proportion of the ingredients. In general, it is preferred that the ratio of the triazine derivative to the aryloxyphenoxy herbicide of formula (IV) is from 10/1 to 1/100 by weight.

The herbicidal composition of the present invention comprises a triazine derivative of formula (1) and a mixture composed of an aryloxyphenoxy herbicide of formula (II) and a safener for crop injury of formula (III) (first composition) or comprises a triazine derivative of formula (I) and an aryloxyphenoxy herbicide of formula (IV) (second composition); and the ingredients are blended with a liquid carrier such as a solvent or a solid carrier such as a mineral powder to be formulated into various forms such as a wettable powder, emulsion, powder, flowable preparation, liquid preparation and others for the practical use of them. For the formulation, surfactants such as an emulsifier, dispersing agent, spreader, suspending agent, penetrating agent and stabilizer and also other various auxiliary additives may be employed.

Where the herbicidal composition of the present invention is used as a form of a wettable powder, in general, from 10 to 55% by weight of the active ingredients comprising, as mentioned above, a triazine derivative of formula (I) and a mixture of an aryloxyphenoxy herbicide of formula (II) and a safener for crop injury of formula (Ill) (as the first composition) or comprising, also as mentioned above, a triazine derivative of formula (I) and an aryloxyphenoxy herbicide of formula (IV) (as the second composition) (they are often referred to simply as active ingredients hereunder), from 40 to 88% by weight of a solid carrier and from 2 to 5% by weight of a surfactant may be blended and formulated into a wettable powder composition for practical use.

Where it is used as a form of an emulsifiable concentrate or a flowable concentrate, in general, from 5 to 50% by weight of the above-mentioned active ingredients, from 35 to 90% by weight of a solvent and from 5 to 15% by weight of a surfactant and other auxiliary additives may be blended and formulated into a preparation of the desired form.

On the other hand, if it is used as a form of a dust, in general, from 1 to 15% by weight of the above-mentioned active ingredients and from 85 to 99% by weight of a solid carrier may be blended and formulated into a dust.

As the solid carrier, usable is a fine powder of a mineral material. Mineral materials include, for example, oxides such as diatomaceous earth, slaked lime and the like; phosphates such as apatite and the like; sulfates such as gypsum and the like; and silicates such as talc, pyrophyllite, clay, kaolin, bentonite, terra alba, white carbon, quartz powder, silica powder and the like.

As the liquid carrier, usable are organic solvents, including, for example, paraffin or naphthene hydrocarbons such as kerosene, mineral oil, spindle oil and the like; aromatic hydrocarbon such as benzene, toluene, xylene and the like; chlorinated hydrocarbons such as o-chlorotoluene, trichloromethane, trichloroethylene and the like; alcohols such as cyclohexanol, amyl alcohol, ethylene glycol and the like; alcohol ethers such as ethylene glycol monomethyl ether, ethylene glycol monoethyl ether and the like; ketones such as isophorone, cyclohexanone, cyclohexenyl-cyclohexanone and the like; ethers such as butyl cellosolve, dimethyl ether, methyl ethyl ether and the like; esters such as isopropyl acetate, benzyl acetate, methyl phthalate and the like; amides such as dimethylformamide and the like; nitriles such as acetonitrile, propionitrile and the like; sulfoxides such as dimethylsulfoxide and the like; and also water.

As the surfactant, usable is anyone of anionic surfactants (e.g., alkylbenzene sulfonates, alkyl sulfonates, lauric acid amide sulfonates, etc.), nonionic surfactants (e.g., polyoxyethylene octyl ethers, polyethylene glycol laurates, sorbitan alkyl esters, etc.), cationic surfactants (e.g., dimethyllaurylbenzylammonium chloride, laurylamine, stearyltrimethylammonium chloride, etc.) and amphoteric surfactants (e.g., amino acids, betaines, etc.).

The herbicidal composition of the present invention may contain high polymer compounds such as sodium alginate, carboxymethyl cellulose, carboxyvinyl polymer, gum arabi, hydroxypropylmethyl cellulose and the like, and other auxiliary agents, so as to improve its property and to elevate its herbicidal effect.

The herbicidal composition of the present invention can be used for weed control in various field crops, such as wheat, barley, oat and the like, by pre- or post-emergence treatment to the soil or the foliage of weeds, and it shows an excellent herbicidal effect against the weeds as a high-selective herbicide with no crop injury. The herbicidal composition shows a high herbicidal effect not only to annual weeds but also to perennial weeds, and it is also extremely effective for weed control in turf or lawn as a high-selective herbicide with no chemical injury to the growing turf.

In addition, the herbicidal composition of the present invention is also usable for blighting weeds in fruits gardens and various non-agricultural areas (plant zone, railway zone, roads, river-side zone, non-cultivated field, etc.) by pre- or post-emergence treatment to the soil or the foliage of weeds.

In practical use, the herbicidal composition of the present invention is applied in an dosage of from 0.1 to 5,000 g, preferably from 1 to 500 g, as the active ingredients, per 10 ares. For spraying the composition over the foliage of weeds, the composition is desired to be diluted to have a concentration of from 1 to 50,000 ppm, preferably from 10 to 5,000 ppm.

The herbicidal composition of the present invention may be combined with any other herbicidal components, if desired. As usable herbicidal components, mentioned are, for example, commercial herbicides such as phenoxyacetic acid compounds, diphenyl ether compounds, triazine compounds, carbamate compounds, thiocarbamate compounds, acid anilide compounds, pyrazole compounds, phosphoric acid compounds, sulfonylurea compounds, imidazolinone compounds, dinitroaniline compounds, bromoxynil, ioxynil, oxadiazone, etc.

In addition, the herbicidal composition of the present invention may be combined, if desired, with an insecticide, a fungicide, a plant growth regulator, a fertilizer, and others.

The present invention will be explained in more detail by way of the following examples, which, however, are not intended to restrict the scope of the present invention.

First, formulation examples are given, concretely explaining the way of producing herbicidal preparations, in which all "parts" are % by weight. As a triazine derivative (compound A), anyone of compounds (A-1 to A-7) shown in Table 1 below was used; as an aryloxyphenoxy herbicide of formula (II), compound B-1 shown in Table 2 below was used; as a safener for crop injury of formula (III), compound C shown in Table 2 was used; and as an aryloxyphenoxy herbicide of formula (IV), compound B-2 in Table 2 was used.

TABLE 1

| Compound | Structural Formula | Chemical Name |
| --- | --- | --- |
| A-1 | | 2-amino-4-[1-(benzofuran-2'-yl)ethylamino]-6-(α-fluoro,α-methylethyl)-s-triazine |
| A-2 | | 2-amino-4-[1-(benzofuran-2'-yl)ethylamino]-6-(α-fluoroethyl)-s-triazine |
| A-3 | | 2-amino-4-[1-(benzothiophen-2'-yl)ethylamino]-6-(α-fluoro,α-methylethyl)-s-triazine |
| A-4 | | 2-amino-4-(α-fluoro,α-methylethyl)-6-[2-(3',5'-dimethylphenoxy)-1-methylethylamino]-s-triazine |
| A-5 | | 2-amino-4-(α-fluoro,α-methylethyl)-6-[2-(3'-fluorophenoxy)-1-methylethylamino]-s-triazine |

TABLE 1-continued

| Compound | Structural Formula | Chemical Name |
|---|---|---|
| A-6 | 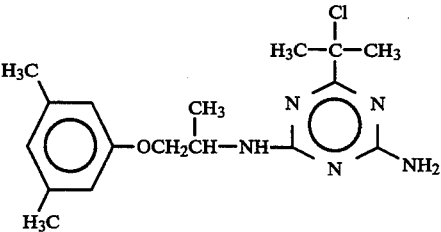 | 2-amino-4-(α-chloro,α-methylethyl)-6-[2-(3',5'-dimethylphenoxy)-1-methylethylamino]-s-triazine |
| A-7 | 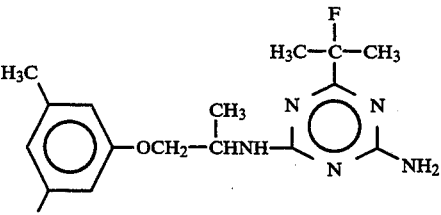 | 2-amino-4-(α-fluoro,α-methylethyl)-6-[2-(3',5'-dimethylphenoxy)-1-methylethylamino]-s-triazine |

TABLE 2

| Compound | Structural Formula | Chemical Name |
|---|---|---|
| B-1 | 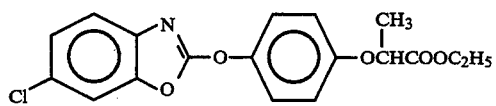 | ethyl-2-[4-(6-chloro-2-benzoxazolyloxy)phenoxy]propionate |
| C | 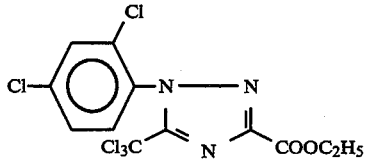 | ethyl-1-(2,4-dichlorophenyl)-5-trichloromethyl-1H-1,2,4-triazole-3-carboxylate |
| B-2 | 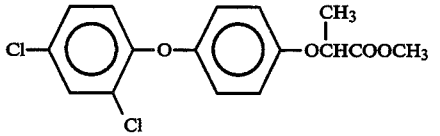 | methyl(1)-2-[4-(2,4-dichlorophenoxy)-phenoxy]propionate |

Formulation Example 1: Wettable Powder

| | |
|---|---|
| Compound A-1 | 5 parts |
| Compound B-1 and Compound C | 15 parts |
| (the former:the latter = 4:1 by weight) | |
| Diatomaceous Earth | 62 parts |
| White Carbon | 15 parts |
| Sodium Alkylbenzenesulfonate | 2 parts |
| Sodium Ligninsulfonate | 1 part |

The above components were uniformly blended and powdered to prepare a wettable powder of 100 parts.

Formulation Example 2: Emulsifiable concentrate

| | |
|---|---|
| Compound A-2 | 10 parts |
| Compound B-2 | 30 parts |
| Xylene | 20 parts |
| Dimethylformamide | 20 parts |
| Solpol 2806B (surfactant produced by Toho Chemical Industry Co.) | 20 parts |

The above components were uniformly blended and emulsified to prepare an emulsifiable concentrate of 100 parts.

Formulation Example 3: Dust

| | |
|---|---|
| Compound A-3 | 0.6 parts |
| Compound B-2 | 1.4 parts |
| Diatomaceous Earth | 20 parts |
| Talc | 78 parts |

The above components were uniformly blended and powdered to prepare a dust of 100 parts.

Formulation Example 4: Flowable concentrate

| | |
|---|---|
| Compound A-7 | 10 parts |
| Compound B-1 and Compound C | 15 parts |
| (the former:the latter = 4:1 by weight) | |
| Methyl Cellulos | 0.3 parts |
| Colloidal Silica | 1.5 parts |
| Sodium Ligninsulfonate | 1 part |
| Polyoxyethylene Nonyl Phenyl Ether | 2 parts |

| | |
|---|---|
| -continued | |
| Water | 70.2 parts |

The above components were uniformly blended and dispersed to give a slurry mixture, and this was wet-milled to obtain a stable flowable concentrate of 100 parts.

Formulation Example 5: Wettable Powder 97 parts of clay (JIKURAITO, trade name by JIKURAITO KOGYO Co.), as a carrier, 1.5 parts of alkylarylsulfonate (Neopelex, trade name by Kao Atlas Co.) as a surfactant and 1.5 parts of a nonionic and anionic surfactant mixture (Solpol 800A, trade name by Toho Chemical Industry Co.) were uniformly blended and powdered to obtain a carrier blend for wettable powder.

90 parts of the carrier blend was uniformly blended with 10 parts of anyone of triazine derivatives (A-1 to A-7) shown in Table 1 above or with 10 parts of a mixture of compound B-1 and C in shown in Table 2 above or with 10 parts of compound B-2 shown in Table 2 alone and powdered to prepare a wettable powder.

Further, the carrier blend containing triazine derivative obtained above was mixed with the carrier containing aryloxyphenoxy herbicide blend (containing mixture of compound B-1 and compound C or containing compound B-2) obtained above in a determined proportion of the active ingredients and powdered to prepare a wettable powder.

EXAMPLE 1

Test on post-emergence treatment

Weed seeds of *Alopecurus myosuroides*, *Galium aparine*, *Veronica hedelifolia* and *Viola arvensis*, and crop seeds of wheat were planted each in 1/2000 ares of Wagner's pots filled with soil, covered with the soil and grown in a greenhouse. A determined amount of the herbicide as obtained in the previous Formulation Example 5 was suspended in water, and the resulting suspension was sprayed uniformly over the foliage of the 1.5-leaves or 2.5-leaves weeds and of the 3-leaves crops at a spray volume corresponding to 100 liters/10 ares. The plants were then grown in the greenhouse. 20 days after the treatment, the crop injury and the herbicidal effect to the weeds were evaluated in accordance with the following criteria. The results obtained are shown in Tables 3-1 and 3-2 below.

TABLE 3-1

| Active Ingredient(s) | Dosage (g/10 a) | Herbicial Effect | | | | Crop Injury |
|---|---|---|---|---|---|---|
| | | Alopecurus myosuroides | Galium aparine | Veronica hedelifolia | Viola arvensis | |
| Triazine Derivative A-1 | 10 | 2 | 2 | 3 | 3 | 0 |
| | 5 | 1 | 1 | 2 | 2 | 0 |
| Triazine Derivative A-2 | 10 | 2 | 3 | 4 | 4 | 0 |
| | 5 | 1 | 2 | 2 | 3 | 0 |
| Triazine Derivative A-3 | 10 | 2 | 3 | 3 | 3 | 0 |
| | 5 | 1 | 1 | 2 | 2 | 0 |
| Triazine Derivative A-4 | 10 | 2 | 3 | 3 | 4 | 0 |
| | 5 | 1 | 2 | 2 | 2 | 0 |
| Triazine Derivative A-5 | 10 | 2 | 3 | 4 | 4 | 0 |
| | 5 | 1 | 2 | 3 | 3 | 0 |
| Triazine Derivative A-6 | 10 | 2 | 3 | 3 | 4 | 0 |
| | 5 | 1 | 1 | 2 | 2 | 0 |
| Triazine Derivative A-7 | 10 | 2 | 4 | 4 | 4 | 0 |
| | 5 | 1 | 2 | 2 | 3 | 0 |
| Herbicide B-1 + Compound C | 8 + 2 | 4 | 3 | 2 | 2 | 0 |
| | 4 + 1 | 2 | 1 | 1 | 1 | 0 |

TABLE 3-2

| Triazine Derivative | | Aryloxyphenoxy Herbicide and Safener for Crop Injury | | Herbicidal Effect | | | | Crop Injury to wheat |
|---|---|---|---|---|---|---|---|---|
| Compound | Dosage (g/10 a) | Compounds | Dosage (g/10 a) | Alopecurus myosuroides | Galium aparine | Veronica hedelifolia | Viola arvensis | |
| A-1 | 10 | mixture of B-1 and C | 8 + 2 | 5 | 5 | 5 | 5 | 0 |
| | 10 | | 4 + 1 | 5 | 5 | 5 | 5 | 0 |
| | 5 | | 8 + 2 | 5 | 5 | 5 | 5 | 0 |
| | 5 | | 4 + 1 | 5 | 5 | 5 | 5 | 0 |
| A-2 | 10 | mixture of B-1 and C | 8 + 2 | 5 | 5 | 5 | 5 | 0 |
| | 10 | | 4 + 1 | 5 | 5 | 5 | 5 | 0 |
| | 5 | | 8 + 2 | 5 | 5 | 5 | 5 | 0 |
| | 5 | | 4 + 1 | 5 | 5 | 5 | 5 | 0 |
| A-3 | 10 | mixture of B-1 and C | 8 + 2 | 5 | 5 | 5 | 5 | 0 |
| | 10 | | 4 + 1 | 5 | 5 | 5 | 5 | 0 |
| | 5 | | 8 + 2 | 5 | 5 | 5 | 5 | 0 |
| | 5 | | 4 + 1 | 5 | 5 | 5 | 5 | 0 |
| A-4 | 10 | mixture of B-1 and C | 8 + 2 | 5 | 5 | 5 | 5 | 0 |
| | 10 | | 4 + 1 | 5 | 5 | 5 | 5 | 0 |
| | 5 | | 8 + 2 | 5 | 5 | 5 | 5 | 0 |
| | 5 | | 4 + 1 | 5 | 5 | 5 | 5 | 0 |
| A-5 | 10 | mixture of B-1 and C | 8 + 2 | 5 | 5 | 5 | 5 | 0 |
| | 10 | | 4 + 1 | 5 | 5 | 5 | 5 | 0 |
| | 5 | | 8 + 2 | 5 | 5 | 5 | 5 | 0 |
| | 5 | | 4 + 1 | 5 | 5 | 5 | 5 | 0 |
| A-6 | 10 | mixture of B-1 and C | 8 + 2 | 5 | 5 | 5 | 5 | 0 |
| | 10 | | 4 + 1 | 5 | 5 | 5 | 5 | 0 |
| | 5 | | 8 + 2 | 5 | 5 | 5 | 5 | 0 |
| | 5 | | 4 + 1 | 5 | 5 | 5 | 5 | 0 |
| A-7 | 10 | mixture of B-1 and C | 8 + 2 | 5 | 5 | 5 | 5 | 0 |
| | 10 | | 4 + 1 | 5 | 5 | 5 | 5 | 0 |
| | 5 | | 8 + 2 | 5 | 5 | 5 | 5 | 0 |

TABLE 3-2-continued

| Triazine Derivative | | Aryloxyphenoxy Herbicide and Safener for Crop Injury | | Herbicidal Effect | | | | Crop Injury to wheat |
|---|---|---|---|---|---|---|---|---|
| Compound | Dosage (g/10 a) | Compounds | Dosage (g/10 a) | Alopecurus myosuroides | Galium aparine | Veronica hedelifolia | Viola arvensis | |
| | 5 | | 4 + 1 | 5 | 5 | 5 | 5 | 0 |

The criteria for evaluation of the herbicidal effects in Tables 3-1 and 3-2 above are as follows:

| Degree of Herbicidal Effect | Herbicidal Rate (percentage of weed control) |
|---|---|
| 0 | less than 5% (almost ineffective) |
| 1 | 5 to 20% |
| 2 | 20 to 40% |
| 3 | 40 to 70% |
| 4 | 70 to 90% |
| 5 | more than 90% (almost completely killed) |

The herbicidal rate (percentage of weed control) was determined according to the following equation, after measuring the weight of the on-the-ground parts in the treated group and that in the non-treated group.

Herbicidal effect (%) =
[1 − (weight of on-the-ground parts in treated group)/ (weight of on-the-ground parts in the non-treated group)] × 100

The crop injury in Tables 3-1 and 3-2 above was determined in accordance with the following 6-rank criteria:

Degree of Crop Injury

0: No injury to crops was observed.
1: Almost no injury to crops was observed.
2: Some injury to crops was observed.
3: Injury to crops was observed.
4: Serious injury to crops was observed.
5: Almost all crops were killed.

EXAMPLE 2

Test on post-emergence treatment

Weed seeds of *Alopecurus myosuroides*, *Galium aparine*, *Veronica hedelifolia* and *Viola arvensis*, and crop seeds of wheat, barley and oat were planted each in 1/2000 are of Wagner's pots filled with soil, covered with soil and grown in a greenhouse. A determined amount of the herbicide as obtained in the previous Formulation Example 5 was suspended in water, and the resulting suspension was sprayed uniformly over the foliage of the 1.5-leaves or 2.5-leaves weeds and of the 3-leaves crops at a spray volume corresponding to 100 liters/10 ares. The plants were then grown in the greenhouse. At 20 days after the treatment, the crop injury and the herbicidal effect to the weeds were evaluated in the same manner as in Example 1. The results obtained are shown in Tables 4-1 and 4-2 below.

TABLE 4-1

| Active Ingredient | Dosage (g/10 a) | Herbicidal Effect | | | | Crop Injury | | |
|---|---|---|---|---|---|---|---|---|
| | | Alopecurus myosuroides | Galium aparine | Veronica hedelifolia | Viola arvensis | wheat | barley | oat |
| Triazine derivative A-1 | 10 | 1 | 2 | 3 | 3 | 0 | 0 | 0 |
| | 5 | 0 | 1 | 2 | 2 | 0 | 0 | 0 |
| Triazine derivative A-2 | 10 | 2 | 3 | 4 | 4 | 0 | 0 | 0 |
| | 5 | 1 | 2 | 2 | 3 | 0 | 0 | 0 |
| Triazine derivative A-3 | 10 | 2 | 3 | 3 | 3 | 0 | 0 | 0 |
| | 5 | 1 | 1 | 2 | 2 | 0 | 0 | 0 |
| Triazine derivative A-4 | 10 | 1 | 3 | 3 | 4 | 0 | 0 | 0 |
| | 5 | 0 | 1 | 2 | 2 | 0 | 0 | 0 |
| Triazine derivative A-5 | 10 | 2 | 3 | 4 | 4 | 0 | 0 | 0 |
| | 5 | 1 | 2 | 3 | 3 | 0 | 0 | 0 |
| Triazine derivative A-6 | 10 | 1 | 3 | 3 | 4 | 0 | 0 | 0 |
| | 5 | 0 | 1 | 2 | 2 | 0 | 0 | 0 |
| Triazine derivative A-7 | 10 | 2 | 4 | 4 | 4 | 0 | 0 | 0 |
| | 5 | 1 | 2 | 2 | 3 | 0 | 0 | 0 |
| Herbicide B-2 | 100 | 4 | 1 | 2 | 2 | 0 | 0 | 0 |
| | 50 | 2 | 0 | 1 | 1 | 0 | 0 | 0 |

TABLE 4-2

| Triazine Derivative | | Aryloxyphenoxy Herbicide | | Herbicidal Effect | | | | Crop Injury | | |
|---|---|---|---|---|---|---|---|---|---|---|
| compound | Dosage (g/10 a) | compound | Dosage (g/10 a) | Alopecurus myosuroides | Galium aparine | Veronica hedelifolia | Viola arvensis | wheat | barley | oat |
| A-1 | 10 | B-2 | 100 | 5 | 5 | 5 | 5 | 0 | 0 | 0 |
| | 10 | | 50 | 5 | 5 | 5 | 5 | 0 | 0 | 0 |
| | 5 | | 100 | 5 | 5 | 5 | 5 | 0 | 0 | 0 |
| | 5 | | 50 | 4 | 4 | 5 | 5 | 0 | 0 | 0 |
| A-2 | 10 | B-2 | 100 | 5 | 5 | 5 | 5 | 0 | 0 | 0 |
| | 10 | | 50 | 5 | 5 | 5 | 5 | 0 | 0 | 0 |
| | 5 | | 100 | 5 | 5 | 5 | 5 | 0 | 0 | 0 |
| | 5 | | 50 | 5 | 5 | 5 | 5 | 0 | 0 | 0 |
| A-3 | 10 | B-2 | 100 | 5 | 5 | 5 | 5 | 0 | 0 | 0 |
| | 10 | | 50 | 5 | 5 | 5 | 5 | 0 | 0 | 0 |

TABLE 4-2-continued

| Triazine Derivative | | Aryloxyphenoxy Herbicide | | Herbicidal Effect | | | | Crop Injury | | |
|---|---|---|---|---|---|---|---|---|---|---|
| compound | Dosage (g/10 a) | compound | Dosage (g/10 a) | Alopecurus myosuroides | Galium aparine | Veronica hedelifolia | Viola arvensis | wheat | barley | oat |
|  | 5 |  | 100 | 5 | 5 | 5 | 5 | 0 | 0 | 0 |
|  | 5 |  | 50 | 5 | 4 | 5 | 5 | 0 | 0 | 0 |
| A-4 | 10 | B-2 | 100 | 5 | 5 | 5 | 5 | 0 | 0 | 0 |
|  | 10 |  | 50 | 5 | 5 | 5 | 5 | 0 | 0 | 0 |
|  | 5 |  | 100 | 5 | 5 | 5 | 5 | 0 | 0 | 0 |
|  | 5 |  | 50 | 4 | 4 | 5 | 5 | 0 | 0 | 0 |
| A-5 | 10 | B-2 | 100 | 5 | 5 | 5 | 5 | 0 | 0 | 0 |
|  | 10 |  | 50 | 5 | 5 | 5 | 5 | 0 | 0 | 0 |
|  | 5 |  | 100 | 5 | 5 | 5 | 5 | 0 | 0 | 0 |
|  | 5 |  | 50 | 5 | 5 | 5 | 5 | 0 | 0 | 0 |
| A-6 | 10 | B-2 | 100 | 5 | 5 | 5 | 5 | 0 | 0 | 0 |
|  | 10 |  | 50 | 5 | 5 | 5 | 5 | 0 | 0 | 0 |
|  | 5 |  | 100 | 5 | 5 | 5 | 5 | 0 | 0 | 0 |
|  | 5 |  | 50 | 4 | 4 | 5 | 5 | 0 | 0 | 0 |
| A-7 | 10 | B-2 | 100 | 5 | 5 | 5 | 5 | 0 | 0 | 0 |
|  | 10 |  | 50 | 5 | 5 | 5 | 5 | 0 | 0 | 0 |
|  | 5 |  | 100 | 5 | 5 | 5 | 5 | 0 | 0 | 0 |
|  | 5 |  | 50 | 5 | 5 | 5 | 5 | 0 | 0 | 0 |

Some samples were picked up from Tables 3-1, 3-2, 4-1 and 4-2 above, and the synergistic herbicidal effect of the respective compositions comprising the triazine derivative (one of A-1 to A-7) and the aryloxyphenoxy herbicide (mixture of B-1 and C or B-2 alone) was examined against weeds of Galium aparine and Viola arvensis. Concretely, the effect was evaluated from the estimated value QE as obtained from the following equation.

$$QE = Qa + Qb - (Qa \cdot Qb/100)$$

For the calculation, L. E. Limpel, P. H. Schuldt and D. Lamont, Proc. NEWCC. 16, 48–53 (1962) was referred to.

If the herbicidal rate (percentage of weed control) of the composition comprising the triazine derivative (one of A-1 to A-7) and the aryloxyphenoxy herbicide (mixture of B-1 and C or B-2 alone) is larger than QE (estimated value), it is concluded that the synergistic herbicidal effect of the composition was attained. The results obtained are shown in Table 5 below.

TABLE 5

| Active Ingredient(s) | Dosage (g/10 a) | Herbicidal rate (%) to Galium aparine | Estimated Value ($Q_E$)(%) | Herbicidal rate (%) to Viola arvensis | Estimated Value ($Q_E$)(%) |
|---|---|---|---|---|---|
| A-1 + (B-1 + C) | 10 + (8 + 2) | 92 | 65 | 94 | 70 |
| A-1 + B-2 | 10 + 100 | 94 | 49 | 96 | 71 |
| A-2 + (B-1 + C) | 5 + (8 + 2) | 96 | 64 | 93 | 64 |
| A-2 + B-2 | 5 + 100 | 92 | 47 | 97 | 65 |
| A-3 + (B-1 + C) | 10 + (8 + 2) | 98 | 74 | 94 | 66 |
| A-3 + B-2 | 10 + 100 | 93 | 62 | 97 | 67 |
| A-4 + (B-1 + C) | 10 + (8 + 2) | 97 | 72 | 98 | 80 |
| A-4 + B-2 | 10 + 100 | 95 | 58 | 99 | 81 |
| A-5 + (B-1 + C) | 5 + (8 + 2) | 96 | 65 | 97 | 63 |
| A-5 + B-2 | 5 + 100 | 92 | 49 | 95 | 64 |
| A-6 + (B-1 + C) | 10 + (8 + 2) | 98 | 75 | 98 | 82 |
| A-6 + B-2 | 10 + 100 | 94 | 63 | 99 | 82 |
| A-7 + (B-1 + C) | 5 + (8 + 2) | 99 | 67 | 97 | 66 |
| A-7 + B-2 | 5 + 100 | 93 | 50 | 95 | 67 |
| A-1 | 10 | 36 | — | 54 | — |
| A-2 | 5 | 34 | — | 46 | — |
| A-3 | 10 | 52 | — | 48 | — |
| A-4 | 10 | 48 | — | 70 | — |
| A-5 | 5 | 36 | — | 44 | — |
| A-6 | 10 | 54 | — | 72 | — |
| A-7 | 5 | 38 | — | 48 | — |
| B-1 + C | 8 + 2 | 46 | — | 34 | — |
| B-2 | 100 | 20 | — | 36 | — | where Qa indicates the herbicidal rate (%), when the active ingredient of only the triazine derivative was used for the treatment in an amount of a g/10 ares; Qb indicates the herbicidal rate (%), when the active ingredient of only the aryloxyphenoxy herbicide of the formula (IV) or the mixture of the aryloxyphenoxy herbicide of the formula (II) and the safener for crop injury was used for the treatment in an amount of b g/10 ares; and QE indicates the estimated value.

EXAMPLE 3

Field Test (post emergence treatment test)

Test fields each having an area of 2 m2 were prepared, and weed seeds of Alopecurus myosuroides, Galium aparine, Stellaria media, Viola arvensis, Matricaria inodora and Veronica hedelifolia, and crop seeds of wheat were planted at the same time.

When weeds grew up to 2–3 leaves stage and when wheat grew up to 3-leaves stage, a determined amount of the dilution of the herbicidal composition obtained in the previous Formulation Example 5 was uniformly sprayed over the foliage of the weeds and the crop at a spray volume corresponding to 20 liters/10 ares.

At 30 days after the treatment, the on-the-ground parts of the weeds were cut out and the weight of them was measured. The herbicidal rate (percentage of weed control) of the composition was obtained from the following equation, as the average of the three test plots. The weight of the on-the-ground parts of the wheat was also measured in the same manner, and the crop injury to them (percentage of crop injury) of the composition was also obtained in the same manner. The results are shown in Table 6 below.

Herbicidal Rate (percentage of weed control) (%) =
[1 − (weight of living weeds in treated test plot)/
(weight of living weeds in the non-treated control plot)] × 100

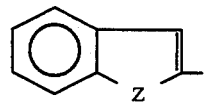

where Z represents an oxygen atom or a sulfur atom, or represents a group of a formula (b):

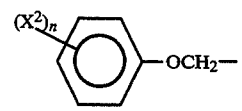

where $X^2$ represents a methyl group or a fluorine atom; and n represents an integer of from 0 to 2; $R^1$ represents a hydrogen atom or a methyl group; and $X^1$ represents a fluorine atom or a chlorine atom; and a mixture of an

TABLE 6

| Active Ingredients | Dosage (g/10 a) | Herbicidal Rate (percentage of weed control) | | | | | | Crop Injury to wheat |
|---|---|---|---|---|---|---|---|---|
| | | Alopecurus myosuroides | Galium aparine | Stellaria media | Viola arvensis | Matricaria inodora | Veronica hedelifolia | |
| A-2 + (B-1 + C) | 20 + (16 + 4) | 100 | 100 | 100 | 100 | 100 | 100 | 0 |
| A-2 + (B-1 + C) | 10 + (16 + 4) | 100 | 100 | 100 | 100 | 100 | 100 | 0 |
| A-2 + B-2 | 20 + 200 | 100 | 100 | 100 | 100 | 100 | 100 | 0 |
| A-2 + B-2 | 10 + 200 | 100 | 100 | 100 | 100 | 100 | 100 | 0 |
| A-7 + (B-1 + C) | 20 + (16 + 4) | 100 | 100 | 100 | 100 | 100 | 100 | 0 |
| A-7 + (B-1 + C) | 10 + (16 + 4) | 100 | 100 | 100 | 100 | 100 | 100 | 0 |
| A-7 + B-2 | 20 + 200 | 100 | 100 | 100 | 100 | 100 | 100 | 0 |
| A-7 + B-2 | 10 + 200 | 100 | 100 | 100 | 100 | 100 | 100 | 0 |

As explained in detail in the above description, the herbicidal composition of the present invention shows a high herbicidal effect even when used in a low dosage, because of the synergistic effect of the active ingredients of the triazine derivative and the aryloxyphenoxy herbicide, and it has a wide range of herbicidal spectrum.

In addition, the herbicidal composition of the present invention shows an excellent activity even to troublesome weeds.

Further, the herbicidal composition of the present invention is highly safe to crops without causing any crop injury to them.

While the invention has been described in detail and with reference to specific embodiments thereof, it will be apparent to one skilled in the art that various changes and modifications can be made therein without departing from the spirit and scope thereof.

What is claimed is:

1. A herbicidal composition comprising, as active ingredients, a triazine compound of a formula (I):

where A represents a group of a formula (a):

aryloxyphenoxy herbicide or, an optical isomer thereof, of a formula (II):

and a safener for crop injury of a formula (III):

wherein the weight ratio of said triazine to said mixture is 10:1 to 1:10.

2. The herbicidal composition as claimed in claim 1, wherein the triazine compound of the formula (I) is a triazine compound selected from the group consisting of 2-amino-4-[1-(benzofuran-2'-yl)ethylamino]-6-(α-fluoro, α-methylethyl)-s-triazine, 2-amino-4-[1-(benzofuran-2'-yl)ethylamino]-6-(α-fluoroethyl)-s-triazine, 2-amino-4-[1-(benzothiophen-2'-yl)ethylamino]-6-(α-fluoro, α-methylethyl)-s-triazine, 2-amino-4-(α-fluoro, α-methylethyl)-6-[2-(3',5'-dimethylphenoxy)-1-methyl-ethylamino]-s-triazine, 2-amino-4-(α-fluoro, α-methylethyl)-6-[2-(3'-fluorophenoxy)-1-methyl-ethylamino]-s-triazine, 2-amino-4-(α-chloro, α-methylethyl)-6-[2-(3',5'-dimethylphenoxy)-1-methylethylamino]-s-triazine and 2-amino-4-(α-fluoro, α-methylethyl)-6-[2-(3',5'-dimethylphenoxy)-1-methyl-ethylamino]-s-triazine.

3. The herbicidal composition as claimed in claim 1, wherein the ratio of the aryloxyphenoxy herbicide of the formula (II) to the safener for crop injury of the formula (III) is from 1/1 to 8/1.

4. A herbicidal composition comprising, as active ingredients, a triazine compound of a formula (I):

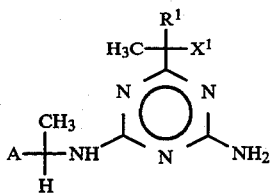

where A represents a group of a formula (a):

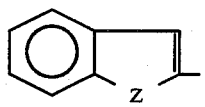

where Z represents an oxygen atom or a sulfur atom, or represents a group of a formula (b):

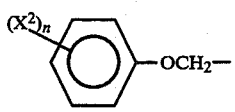

where $X^2$ represents a methyl group or a fluorine atom; and n represents an integer of from 0 to 2; $R^1$ represents a hydrogen atom or a methyl group; and $X^1$ represents a fluorine atom or a chlorine atom; and an aryloxyphenoxy herbicide of a formula (IV):

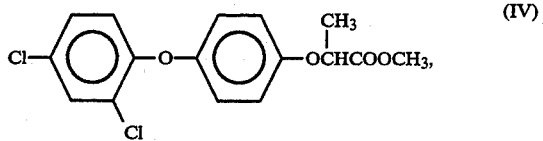

wherein the weight ratio of the triazine compound to the aryloxyphenoxy herbicide of the formula (IV) is 10/1 to 1/100.

5. The herbicidal composition as claimed in claim 4, wherein the triazine compound of the formula (I) is a triazine compound selected from the group consisting of 2-amino-4-[1-(benzofuran-2'-yl)ethylamino]-6-(α-fluoro, α-methylethyl)-s-triazine, 2-amino-4-[1-(benzofuran-2'-yl)ethylamino]6-(α-fluoroethyl)-s-triazine, 2-amino-4-[1-(benzothiophen-2'-yl)ethylamino]-6-(α-fluoro, α-methylethyl)-s-triazine, 2-amino-4-(α-fluoro, α-methylethyl)-6-[2-(3',5'-dimethylphenoxy)-1-methyl-ethylamino]-s-triazine, 2-amino-4-(α-fluoro, α-methylethyl)-6-[2-(3'-fluorophenoxy)-1-methyl-ethylamino]-s-triazine, 2-amino-4-(α-chloro, α-methylethyl)-6-[2-(3',5'-dimethylphenoxy)-1-methylethylamino]-s-triazine and 2-amino-4-(α-fluoro, α-methylethyl)-6-[2-(3',5'-dimethylphenoxy)-1-methyl-ethylamino]-s-triazine.

6. The herbicidal composition as claimed in claim 2, wherein the weight ratio of said aryloxyphenoxy herbicide to said safener is 1/1 to 8/1.

7. The herbicidal composition as claimed in claim 2, wherein the weight ratio of said aryloxyphenoxy herbicide to said safener is 2/1 to 4/1.

8. The herbicidal composition as claimed in claim 5, wherein the weight ratio of said triazine compound to said aryloxyphenoxy herbicide is 10/1 to 1/100.

9. A method of combatting weeds comprising applying to weeds or to a locus thereof, an effective herbicidal amount of the herbicidal composition as claimed in claim 1.

10. The method as claimed in claim 9, wherein said triazine compound is selected from the group consisting of 2-amino-4-[1-(benzofuran-2'-yl)ethylamino]-6-(α-fluoro, α-methylethyl)-s-triazine, 2-amino4-[1-(benzofuran-2'-yl)ethylamino]-6-(α-fluoroethyl)-s-triazine, 2-amino-4-[1-(benzothiophen-2'-yl)ethylamino]-6-(α-fluoro, α-methylethyl)-s-triazine, 2-amino-4-(α-fluoro, α-methylethyl)-6-[2-(3',5'-dimethylphenoxy)-1-methyl-ethylamino]-s-triazine, 2-amino-4-(α-fluoro, α-methylethyl)-6-[2-(3'-fluorophenoxy)-1-methyl-ethylamino]-s-triazine. 2-amino-4-(α-chloro, α-methylethyl)-6-[2-(3',5'-dimethylphenoxy)-1-methylethylamino]-s-triazine and 2-amino-4-(α-fluoro, α-methylethyl)-6-[2-(3',5'-dimethylphenoxy)-1-methyl-ethylamino]-s-triazine.

11. The method as claimed in claim 10, wherein the weight ratio of said aryloxyphenoxy herbicide to said safener is 1/1 to 8/1.

12. A method of combatting weeds comprising applying to weeds or a locus thereof, an effective herbicidal amount of the herbicidal composition as claimed in claim 4.

13. The method as claimed in claim 12, wherein said triazine compound is selected from the group consisting of 2-amino-4-[1-(benzofuran-2'-yl)ethylamino]-6-(α-fluoro, α-methylethyl)-s-triazine, 2-amino-4-[1-(benzofuran-2'-yl)ethylamino]-6-(α-fluoroethyl)-s-triazine, 2-amino-4-[1-(benzothiophen-2'-yl)ethylamino]-6(α-fluoro, α-methylethyl)-s-triazine, 2-amino-4-(α-fluoro, α-methylethyl)-6-[2-(3',5'-dimethylphenoxy)-1-methyl-ethylamino]-s-triazine, 2-amino-4-(α-fluoro, α-methylethyl)-6-[2-(3'-fluorophenoxy)-1-methyl-ethylamino]-s-triazine, 2-amino-4-(α-chloro, α-methylethyl)-6-[2-(3',5'-dimethylphenoxy)-1-methylethylamino]-s-triazine and 2-amino-4-(α-fluoro, α-methylethyl)-6-[2-(3',5'-dimethylphenoxy)-1-methyl-ethylamino]-s-triazine.

* * * * *